United States Patent [19]

Kiely et al.

[11] Patent Number: 5,329,044

[45] Date of Patent: Jul. 12, 1994

[54] GLUCARIC ACID MONOAMIDES AND THEIR USE TO PREPARE POLY(GLUCARAMIDES)

[76] Inventors: Donald E. Kiely, 2521 Chatwood Rd., Birmingham, Ala. 35226; Liang Chen, 206 Vail Ave. #217, Birmingham, Ala. 35209

[21] Appl. No.: 928,007

[22] Filed: Aug. 12, 1992

[51] Int. Cl.$^5$ ............................................. C07C 229/00
[52] U.S. Cl. .................................... 562/564; 562/426; 562/450; 562/556; 528/335
[58] Field of Search ................ 562/564, 426, 450, 556

[56] References Cited

U.S. PATENT DOCUMENTS 4,833,230  5/1989  Kiely ..................................... 528/230
4,975,441  12/1990  Gibson ................................ 514/328

OTHER PUBLICATIONS

Lee, Carbohydrate Research, 64, pp. 302-308 (1978).
Zinner et al., Chem. Abs. 51, 5704-5 (1956).

Primary Examiner—Michael L. Shippen
Attorney, Agent, or Firm—Glenna Hendricks; Stephen Gates

[57] ABSTRACT

Novel monomers are described which contain a glucaric acid unit linked through an amide bond formed between a carbonyl carbon of a D-glucaric acid and one of the amino nitrogens of a primary diamine as well as their alkali metal salts. These N-aminohydrocarbylene (or N-aminoheterohydrocarbylene)-D-glucaramidates may then be polymerized to form polyhydroxypolyamides and in particular stereoregular polyhydroxypolyamides.

4 Claims, No Drawings

GLUCARIC ACID MONOAMIDES AND THEIR USE TO PREPARE POLY(GLUCARAMIDES)

The present invention is directed to a general process for preparing glucaric acid monoamides and the use of the amides to prepare polyhydroxypolyamides and in particular stereoregular head, tail-polyhydroxypolyamides based upon chiral glucaric acid as the diacid monomer unit and symmetrical diamines.

BACKGROUND OF THE INVENTION

Kiely and coworkers in U.S. Pat. No. 4,833,230 and copending application "An Improved Process for Making Activated Aldarate Esters, Ester/Lactones" of even date herewith describe general methods for preparing polyhydroxypolyamides from aldaric acids, including poly(glucaramides) from D-glucaric acid. In that process, activated glucaric acid molecules are reacted with diamines via condensation polymerization to produce poly(glucaramides).

The D-glucaric acid monomer units (I) in a poly(glucaramide)

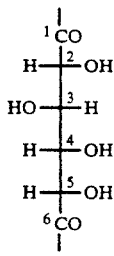

are not symmetrical. The C-2 to C-5 carbon atoms in the D-glucaric acid are chiral carbons and employing the Cahn-PrelogIngold Sequence Rules are configurationally designated as R,C-2-S,C-3- S,C-4 - S,C-5. C-1 is labelled as the "head" carbon in the D-glucaric acid and C-6 is labelled as the "tail" carbon in the D-glucaric acid monomer unit. The process of Kiely et al. does not indicate nor ensure the order in which the glucaric acid units are placed in the poly(glucaramide); i.e. the method of synthesis does not control that stereoregularity of the condensation process. Consequently, the resulting polymers would be expected to have a random or somewhat random head-tail order of a D-glucaric acid unit with respect to other D-glucaric acid units within the polymer. Stereoregular head to tail poly(glucaramides) containing D-glucaric acid units aligned—[tail-glucaroyl-head—amine]—$_n$, where "glucaroyl" is (I) above, have not been described in the art.

SUMMARY OF THE INVENTION

This invention provides novel monomers which contain a glucaric acid unit linked through an amide bond formed between a carbonyl carbon of a D-glucaric acid and one of the amino nitrogens of a primary diamine as well as their alkali metal salts. These N-aminohydrocarbylene (and N-aminoheterohydrocarbylene)-D-glucaramidate units have the general formula

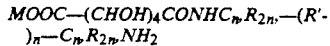

wherein

M is an alkali metal or hydrogen;

each R is individually selected from the group comprising hydrogen, alkyl, alkenyl, aryl, aryl-substituted alkyl and alkenyl, and alkyl- and alkenyl-substituted aryl;

R' is a hydrocarbylene radical selected from the group comprising alkylene, alkenylene, aryl- and alkyl-substituted alkylene and alkenylene, arylene, alkyl- and alkenyl-substituted arylene and R'';

R'' is a heterohydrocarbylene radical (R'XR''')$_{n''}$ wherein

R' is designated as above;

each R''' is individually R' or a valence bond;

X is selected from the group comprising —O—, —S—, —NR''''—and PR'''', wherein R'''' is selected from the group comprising hydrogen alkyl, alkenyl, aryl, aralkyl and alkaryl;

n is zero or 1;

each n' has a value of at least 1; and n'' is an integer.

The N-aminohydrocarbyleneglucaramidates and N-aminoheterohydrocarbyleneglucaramidates may then be polymerized to form polyhydroxypolyamides and stereoregular polyhydroxypolyamides in particular. (The corresponding L-glucaramides would be available from L-glucaric acid.) The repeating N-aminohydrocarbylene (or N-aminoheterohydrocarbylene)-D-glucaramido monomer units in the polymer are derived from alkali metal N-aminohydrocarbylene (or N-aminoheterohydrocarbylene)-D-glucaramidates which are then activated and self condensed to form the corresponding poly(hydrocarbyleneglucaramides) or poly(heterohydrocarbyleneglucaramides) through connection of the C-1 or C-6 carbonyl carbon of the monomer respectively with the C-6 or C-1 terminal amine group of a second monomer by formation of a amide bond. When the diamine is symmetrical the process yields stereoregular polymers.

DETAILED DESCRIPTION OF THE INVENTION

The novel alkali metal N-aminohydrocarbyl- and N-aminoheterohydrocarbyl-D-glucaramidates suitable for activation to monomers for the self condensation polymerization process are prepared by reacting an alkali metal D-glucarate 6,3-lactone or D-glucarate 1,4-lactone in a polar solvent such as methanol, ethanol, isopropanol, ethylene glycol, a lower alkyl ether, dioxane, tetrahydrofuran, dimethylformamide, dimethylsulfoxide or the like or mixtures thereof with a diprimary diamine in which the nitrogen atoms are connected to aliphatic carbon atoms. When a high purity monomer is desired for making stereoregular polymer an excess of a symmetrical diamine is usually used. A substantial molar excess of amine may be necessary in order to minimize the occurrence of two molecules of lactone reacting with the same molecule of amine. The molar excess employed is not critical, but may be of the order of 3:1 or more. The insoluble amide salts are readily isolated from the excess diamine and solvent by filtration. When an excess of diamine has been used the solvent solution may be recycled to the process for preparing additional amide salt, or it may be separated from the solvent and recovered by means well-understood in the art.

The alkali metal N-aminohydrocarbyl- or N-aminoheterohydrocarbyl-D-glucaramidate may then be reacted with an alkanol containing a strong acid to form a C-6 (when starting with the 1,4-lactone) or C-1 (when starting with the 6,3-lactone) esterified amine terminated base as its ammonium salt. Suitable alkanols include but are not limited to lower alkanols such as methanol, ethanol, propanol, isopropanol and the like. Methanol and ethanol are preferred because of their low cost and volatility. The strong acid preferably is sufficiently volatile to allow it to be removed readily when the reaction is completed. The use of HCl/alkanol has been found to be particularly convenient. On a small scale it is convenient to generate the HCl in situ by adding acetyl chloride to the alcohol to be used in the esterification. This esterification or activation is followed by removal of excess alkanol and acid at reduced pressure. Basification of the residue in a solvent (generally a polar solvent, e.g. methanol) produces the ester/lactone - amine monomer, (i.e., a 6-(N-aminohydrocarbyl)-D-glucaramid-1-ate or a 1-(N-aminohydrocarbyl)-D-glucaramid-6-ate monomer or the corresponding heterohydrocarbyl monomer) which spontaneously polymerizes. Copolymers may be prepared by this process by simply using a mixture of glucaramidate salts in the desired proportions. When the glucaramidate salt has been prepared using an excess of symmetrical diamine this reaction sequence ensures that the order of condensation generates head, tail-poly(hydrocarbyleneglucaramides) and poly(heterohydrocarbyleneglucaramides).

Primary diamines and polyamines suitable for use in practice of the invention are amines in which the nitrogen atoms are bound to aliphatic carbon atoms. Diamines include hydrocarbylenediamines and heterohydrocarbylenediamines. The hydrocarbylenediamines are alkylene and aralkylene diamines having the general formula

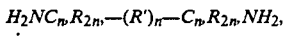

$H_2NC_{n'}R_{2n'}-(R')_n-C_{n'}R_{2n'}NH_2$, wherein each R is individually selected from the group comprising hydrogen, alkyl, alkenyl, aryl, aryl-substituted alkyl and alkenyl, and alkyl- and alkenyl-substituted aryl;

R' is selected from the group comprising alkylene, alkenylene, aryl- and alkyl-substituted alkylene and alkenylene, arylene, alkyl- and alkenyl-substituted arylene;

n is zero or 1; and each n' has a value of at least 1.

The heterohydrocarbylenediamines are diamines having the general formula

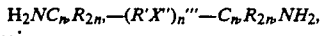

$H_2NC_{n'}R_{2n'}-(R'X'')_{n'''}-C_{n'}R_{2n'}NH_2$, wherein

R, R' and n' are designated as above;

each R'' is individually R' or a valence bond;

X is selected from the group comprising —O—, —S—, —NR'''—and PR''', wherein R''' is selected from the group comprising hydrogen, alkyl, alkenyl, aryl, aralkyl and alkaryl; and n''' may be 0 or an integer.

Examples of diamines include but are not limited to: alkylenediamines such as ethylenediamine, hexamethylenediamine, 2-methylpentamethylenediamine, 2-phenyltetramethylenediamine and the like; aralkyldiamines such as o-, m- and p-xylylenediamine, ar-alkyl substituted xylylenediamines and the like; and heteroalkylene diamines such as polyoxyethylenediamine, polyoxypropylene diamine, 4-aza-4-octylheptamethylenediamine, 4-phospha-4-ethylheptamethylenediamine, polythioethylenediamine and the like.

Examples of hydrocarbylenediamines include but are not limited to: alkylenediamines such as ethylenediamine, hexamethylenediamine, 2-methylpentamethylenediamine, 2-phenyltetramethylenediamine and the like; aralkyldiamines such as o-, m- and p-xylylenediamine; ar-alkyl substituted xylylenediamines and the like. Heterohydrocarbylenediamines include but are not limited to polyoxyethylenediamines, polyoxypropylenediamines, 4-aza-4-octylheptamethylenediamine, 4-phospha-4-ethylheptamethylenediamine, polythioethylenediamines and the like.

In order to prepare stereoregular polymers the amino nitrogens of the diamines must be equivalent to each other. Such diamines include but are not limited to the simple symmetrical polyalkylene diamines such as ethylenediamine, trimethylenediamine, tetramethylenediamine, pentamethylenediamine, hexamethylenediamine, octamethylenediamine, decamethylenediamine, dodecamethylenediamine, o- m- or p-xylylenediamine, 3,6-dioxaoctamethylenediamine, 4-aza-4-methylheptamethylenediamine and the like. If unsymmetrical diamines such as 2-methylpentamethylene diamine and the like are used, the resulting polymers will not be stereoregular because there are no means to ensure which of the non-equivalent amino nitrogens will react with the glucarolactone in the monomer forming step.

The invention thus provides monomers useful in a general process for preparing polyhydroxypolyamides. It is particularly useful in providing monomers which will yield stereoregular polyhydroxypolyamides based upon chiral glucaric acid as the diacid monomer unit with symmetrical diamines.

The precursor form of the monomer for the polymerization, an alkali metal N-aminohydrocarbyl- (or heterohydrocarbyl)-D-glucaramidate prepared from a D-glucaro-6,3-lactone or a D-glucaro-1,4-lactone contains a glucaric acid unit linked through an amide bond between a specific carbonyl carbon of a D-glucaric acid and an amine nitrogen of a diamine.

The polymers of the invention may be used as films for industrial, agricultural, pharmaceutical, medicinal, health care and personal care purposes. Film forming uses include biodegradable films for disposable health care products (e.g. disposable diapers, sanitary napkins and other biological fluid absorbents), biodegradable disposable packaging materials, and biodegradable disposable trash bags. Other uses include use as chemicals/polymers in the manufacture of paper. Uses in textiles include use as antistatic agents in textiles for manufacturing fabrics with antistatic characteristics, as hydrophilic fibers and/or components of hydrophilic fibers, as water permeable nylons and/or components of water permeable nylons, polyesters and polyacrylonitriles and/or other common synthetic polymers for manufacture of water permeable fabrics and/or membranes. The polymers may also have use as components of biodegradable agriculture mulches, biodegradable time release fertilizers, biodegradable encapsulation materials for chemical agents used in agriculture [agricultural biocides in general (including pesticides and plant virucides)], fertilizers and other agricultural chemical agents where time release is important for best use. Other developing uses of the polymers include in adhesives, industrial and municipal water treatment (e.g. biodegradable flocculating agents and materials for concentration of heavy metal ions), and biodegradable absorbent materials for use in human fluid absorption (urine and blood). Some applications will use the polymers physically or chemically combined with other materials such as biopolymers (starch and/or derivatives, cellulose and/or derivatives, guar and/or derivatives, chitin and/or derivatives and other common industrial polysaccharides and/or derivatives), synthetic polymers (nylons, polyacrylic acid and/or derivatives, polyethylene and polypropylene and/or derivatives and other common synthetic polymers). The biodegradable polymers can also contain photodegradable segments rendering polymers with both photo- and biodegradable characteristics. Such polymers can be employed for purposes (from above and others) that would take advantage of both characteristics. Other uses of the polymers are as biocides and pesticides in agricultural, specialty industrial membranes and biomembranes, components of cosmetic products [e.g. polymeric quaternary ammonium salts and/or polymers with amphoteric nitrogens (i.e. zwitterionic) in the polymer, emulsifiers, softeners etc.], polymers or derivatives for use as chromatographic column materials in general and in particular for separating racemic mixtures (e.g. racemic drug mixtures, drugs, bioactive compounds and others) into component enantiomers. The polymers can also serve as surfactants and detergents and as other functional components (e.g. builders, softeners and others) in detergent preparations. The chirality of the polymers may make them useful in non-linear optical materials. Additional uses can be envisioned which would particularly utilize the special properties of the stereoregular polymers of the invention.

EXPERIMENTAL

General methods. All $^1$H and $^{13}$C NMR spectra were recorded using a GE 300WB FT-NMR spectrometer at 300.13 Mhz and 75.4 MHz respectively. Chemical shifts are reported as ppm ($\delta$) downfield from tetramethylsilane (TMS) or sodium 2,2,3,3-tetradeuterio-3-trimethylsilyl propionate (TSP). IR spectra were recorded with a Nicolet IR42 FT IR spectrometer as KBr pellets. All solvents used were reagent grade unless stated otherwise. Melting points were recorded with a Fisher-Johns Melting Point Apparatus and are reported uncorrected. Solvent evaporations were carried out at reduced pressure.

EXAMPLE 1

D-Glucaro-6,3-lactone. Acid form cation exchange resin (20 mL, 40 meq. of total exchange capacity, Rexyn 100(H), Fisher) that had been prewashed with deionized water was added to a mixture of monopotassium D-glucarate (10.00 g, 39.89 mmol, Sigma) and deionized water (100 mL). The potassium salt dissolved within 10 min, the mixture was stirred for 3 h and the resin was removed by filtration and washed with deionized water (3×10 mL). The resin was left aside for regeneration to its acid form and the filtrate was concentrated to a syrup at 60 ° C. The syrup was seeded with pure D-glucaro-3,6-lactone and solidified as a cake in two - three days. The cake was triturated with acetone (15 mL), the white solid was removed by filtration and air-dried to yield D-glucaro-6,3-lactone (4.851 g, 63.3%). When this experiment was scaled up to 50.00 g of monopotassium D-glucarate, D-glucaro-6,3-lactone was obtained in 69.1% yield (26.49 g, 137.9 mmol): mp 130°-135° C. [Smith, *J. Chem. Soc.*, 633 (1944); 138°-142° C.]; IR (KBr) 3365 cm$^{-1}$ (broad, OH), 2913 cm$^{-1}$ (C-H, stretch), 1780 cm$^{-1}$ (C=O, five membered ring lactone), 1725 cm$^{-1}$ (C=O, acid); $^1$H NMR (CD$_3$OD) $\delta$ 4.59 (dd, 1H, H-3, $J_{2,3}$=6.73 Hz, $J_{3,4}$=2.12), 4.53 (m, 2H, H-2, H-5,), 4.51 (m, 1H, H-2); proton decoupled $^{13}$C NMR (D$_2$O) $\delta$ 178.8 (lactone C=O), 174.5 (acid C=O), 81.61 (C-3), 71.65 (C-5), 71.31 (C-2), and 69.89 (C-4).

Anal. Calcd for C$_6$H$_8$O$_7$ (192.1): C, 37.51; H, 4.20. Found: C, 37.18; H, 4.16.

EXAMPLE 2

Sodium D-glucarate 6,3-lactone. Sodium acetate (2. 125 g, 15.62 mmol, CH$_3$COONa·3H$_2$O, FW 136.08, Fisher) was added to a solution of D-glucaro-6,3-lactone (3.000 g, 15.62 mmol) in deionized water (10 mL). White crystals began to form within 20 min after scratching the wall of the reaction glass. The solution was set aside without stirring at room temperature for 6 h. The crystalline product was removed by filtration and washed with acetone (3×5 mL). Additional product crystallized from the aqueous acetone over 2 h and was combined with the first crop of crystals. The acetone washings, crystallization and filtration process was repeated once more and the combined white solids were dried at reduced pressure (0.25 torr) and 50° C. to give sodium D-glucarate 6,3-lactone (2.595 g, 12.1 mmol, 77.6%): mp 180° C. (dec.); IR (KBr) 3292 cm$^{-1}$ (broad, OH), 2860 cm$^{-1}$ (C-H, stretch), 1782 cm$^{-1}$ (C=O stretch, five membered lactone), 1597 cm$^{-1}$ (C=O stretch, carboxylate); proton decoupled $^{13}$C NMR (D$_2$O) $\delta$ 177.34 (C=O, lactone), 175.50 (C=O, carboxylate), 81.61 (C-3), 70.50 (C-5), 69.53 (C-2 and C-4); $^1$H NMR (D$_2$O) $\delta$ 4.765 (d, 1H, H-2, $J_{2,3}$=5.1 Hz), 4.626 (m, 2H, H-3 and H-5), 4.392 (m, 1H, H-4).

Anal. Calcd for C$_6$H$_7$O$_7$Na (214.11): C, 33.67; H, 3.30; Na, 10.74. Found: C, 33.42; H, 3.35; Na, 10.61.

EXAMPLE 3

Sodium 6-[N-(2'-aminoethyl)]glucaramide-1-ate. A mixture of finely ground sodium D-glucarate 6,3-lactone (0.6000 g, 2,802 mmol), methanol (12 mL) and ethylenediamine (6 mL, 89.7 retool) in a 100 mL round-bottomed flask was refluxed for 3 h at an oil bath temperature of 95 ° C. During reflux, the amount of insoluble white solid in the reaction mixture appeared to increase. The mixture was cooled to room temperature, the white solid removed by filtration, washed with methanol (2×10 mL), acetone (2×10 mL) and dried at reduced pressure (0.25 torr) at 60° C. for 6 h to give sodium 6-[N-(2'-aminoethyl) ]glucaramide-1-ate (0. 7044 g, 2.57 mmol, 91.7%): mp 195°-299° C. (dec.); IR (KBr) 3412 cm$^{-1}$ (N-H, stretch), 3170 cm$^{-1}$ (O-H, stretch), 1664 cm$^{-1}$ (Amide I, C=O stretch), 1620 cm$^{-1}$ (COO$^-$ and amine N-H bend overlapping), 1517 cm$^{-1}$ (Amide II, N-H bend); $^1$H NMR (D$_2$O) $\delta$ 4.15 (d, 1H, H-2, $J_{2,3}$=3.14 Hz), 4.07 (dd, 1H, H-3), 3.96 (dd, 1H, H-4, $J_{4,5}$=5.35 Hz), 4.27 (d, 1H, H-5), 3.34 (t, 2H, H-1', $J_{1',2'}$=6.0 Hz), 2 77 (t, 2H, H-2').

Anal. Calcd for C$_8$H$_{15}$O$_7$N$_2$Na: C, 35.04; H, 5.52; N, 10.21; Na, 8.38. Found: C, 35.01; H, 5.51; N, 10.12; Na, 8.29.

EXAMPLE 4

Sodium 6-[N-(4'-aminobutyl)]glucaramide-1-ate. A mixture of finely ground sodium D-glucarate 6,3-lactone (2.000 g, 9.342 mmol), methanol (50 mL), and tetramethylenediamine (5.0 mL, 49.7 mmol) in a 250 mL round-bottomed flask was refluxed for 3 h at an oil bath temperature of 95 °C. During reflux, the amount of insoluble white solid in the reaction mixture appeared to increase. The mixture was cooled to room temperature, the white solid removed by filtration, washed with methanol (2×10 mL), acetone (2×10 mL) and dried at reduced pressure (0.25 torr) at 60° C. for 6 h to give sodium 6-[N-(4′-aminobutyl)]glucaramide-1-ate (2.679 g, 8.863 retool, 94.9%): mp 205°–208° C. (dec.); IR (KBr) 3396 cm$^{-1}$ and 3343 cm$^{-1}$ (N-H, stretch), 3169 cm$^{-1}$ (O-H, stretch), 1659 cm$^{-1}$ (Amide I, C=O), 1613 cm$^{-1}$ (COO$^-$ and amine), 1522 cm$^{-1}$ (Amide II, N-H bend); $^1$H NMR (D$_2$O) δ 4.13 (d, 1H, H-2, $J_{2,3}$=3.10 Hz), 4.06 (t, 1H, H-3), 3.97 (t, 1H, H-4, $J_{4,5}$=5.33 Hz), 4.25 (d, 1H, H-5), 3.27 (t, 2H, H-1′, $J_{1',2'}$=6.0 Hz), 1.55 (m, 4H, H-2′, H-3′), 2.67 (t, 2H, H-4′, $J_{3',4'}$=6.7 Hz).

Anal. Calcd for C$_{10}$H$_{19}$O$_7$N$_2$Na: C, 39.73; H, 6.34; N, 9.27; Na, 7.62. Found: C, 39.69; H, 6.38; N, 9.24; Na, 7.54.

EXAMPLE 5

Sodium 6-[N-(6′-aminohexyl)]glucaramide-l-ate. A mixture of finely ground sodium D-glucarate 6,3-lactone (0.5000 g, 2,335 mmol), methanol (30 mL) and hexamethylenediamine (5.0 g, 43.02 mmol) in a 100 mL round-bottomed flask was refluxed for 3 h at an oil bath temperature of 95° C. During reflux, the amount of insoluble white solid in the reaction mixture appeared to increase. The mixture was cooled to room temperature, the white solid removed by filtration, washed with methanol (2×10 mL), acetone (2×10 mL) and dried at reduced pressure (0.25 torr) at 60° C. for 6 h to give sodium 6-[N-(6′-aminohexyl)]glucaramide-1-ate (0.7013 g, 2.12 mmol, 90.9%): mp 209°–212 ° C. (dec.); IR (KBr) 3393 cm$^{-1}$ and 3341 cm$^{-1}$ (N-H, stretch), 3167 cm$^{-1}$ (O-H, stretch), 1655 cm$^{-1}$ (Amide I, C=O), 1625 cm$^{-1}$ (COO$^-$ and amine N-H bend), 1519 cm$^{-1}$ (Amide II, N-H bend); $^1$H NMR (D$_2$O) δ 3.93 (d, 1H, H-2, $J_{2,3}$=2.63 Hz), 3.86 (t, 1H, H-3), 3.77 (t, 1H, H-4, $J_{4,5}$=4.89 Hz) , 4.04 (d, 1H, H-5), 3.05 (t, 2H, H-1′, $J_{1',2'}$=6.6 Hz), 2.44 (t, 2H, H-6′, $J_{5',6'}$=6.9 Hz), 1.35 (m, 2H, H-2′), 1 26 (m, 2H, H-5′), 1.14 (s, 4H, H-3′ and H-4′).

Anal. Calcd for C$_{12}$H$_{23}$O$_7$N$_2$Na: C, 43.63; H, 7.03; N, 8.48; Na, 6.96. Found: C, 43.61; H, 7.06; N, 8.37; Na, 6.94.

EXAMPLE 6

Sodium 6-[N-(8′-aminooctyl)]glucaramide-1-ate. A mixture of finely ground sodium D-glucarate 6,3-lactone (1,000 g, 4,671 mmol), methanol (30 mL) and octamethylenediamine (3.37 g, 23.4 mmol) in a 100 mL round-bottomed flask was refluxed for 3 h at an oil bath temperature of 95° C. During reflux, the amount of insoluble white solid in the reaction mixture appeared to increase. The mixture was cooled to room temperature, the white solid removed by filtration, washed with methanol (2×10 mL), acetone (2×10 mL) and dried at reduced pressure (0.25 torr) at 60° C. for 6 h to give sodium 6-[N-(8′-aminooctyl)]glucaramide-1-ate (1.570 g, 4.38 mmol, 93.8%): mp 205°–208° C.; IR (KBr) 3392 cm$^{-1}$ (N-H, stretch), 3165 cm$^{-1}$ (O-H, stretch), 1654 cm$^{-1}$ (Amide I, C=O), 1627 cm$^{-1}$ (COO$^-$ and amine bend), 1517 cm$^{-1}$ (Amide II, N-H bend); $^1$H NMR (D$_2$O) δ 4.13 (d, 1H, H-2, $J_{2,3}$=3.01 Hz), 4.06 (t, 1H, H-3, $J_{3,4}$=4.44 Hz), 3.97 (dd, 1H, H-4, $J_{4,5}$=5.03 Hz), 4.24 (d, 1H, H-5), 3.25 (t, 2H, H-1′, $J_{1',2'}$=6.6 Hz), 2 68 (t, 2H, H-8′, $J_{7',8'}$=7.2 Hz), 1.48 (m, 4H, H-2′ and H-7′), 1.32 (s, 8H, H-3′, H-4′, H-5′, and H-6′).

Anal. Calcd for C$_{14}$H$_{27}$O$_7$N$_2$Na (358.4): C, 46.92; H, 7.60; N, 7.82; Na, 6.41. Found: C, 46.70; H, 7.55; N, 7.78; Na, 6.46.

EXAMPLE 7

Sodium 6-[N-(10′-aminodecyl)]glucaramide-1-ate. A mixture of finely ground sodium D-glucarate 6,3-lactone (1,000 g, 4,671 mmol), methanol (30 mL) and decamethylenediamine (5.00 g, 29.0 mmol) in a 100 mL round-bottomed flask was refluxed for 3 h at an oil bath temperature of 95 °C. During reflux, the amount of insoluble white solid in the reaction mixture appeared to increase. The mixture was cooled to room temperature, the white solid removed by filtration, washed with methanol (2×10 mL), acetone (2×10 mL) and dried at reduced pressure (0.25 torr) at 60° C. for 6 h to give sodium 6-[N-(10′-aminodecyl)]glucaramide-1-ate (1.630 g, 4.22 mmol, 90.3%): mp 195°–198° C.; IR (KBr) 3391 cm$^{-1}$ and 3338 cm$^{-1}$ (N-H, stretch), 3165 cm$^{-1}$ (O-H, stretch), 1653 cm$^{-1}$ (Amide I, C=O), 1628 cm$^{-1}$ (COO$^-$ and amine N-H bend), 1518 cm$^{-1}$ (Amide II, N-H bend); $^1$H NMR (D$_2$O) δ 4.14 (d, 1H, H-2, $J_{2,3}$=3.18 Hz), 4.06 (t, 1H, H-3), 3.96 (t, 1H, H-4, $J_{4,5}$=5.36 Hz), 4.24 (d, 1H, H-5), 3 24 (t, 2H, H-1′, $J_{1',2'}$=6.77), 2.69 (t, 2H, H-10′, $J_{9',10'}$=7.10 Hz), 1.50 (m, 4H, H-2′ and H-9′), 1.30 (s, 12H, H-3′, H-4′, H-5′, H-6′, H-7′, and H-8′).

Anal. Calcd for C$_{16}$H$_{31}$O$_7$N$_2$Na (386.46): C, 49.73; H, 8.10; N, 7.25; Na, 5.95. Found: C, 49.45; H, 7.96; N, 7.23; Na, 5.99.

EXAMPLE 8

Sodium 6-[N-(12′-aminododecyl)]glucaramide-1-ate. A mixture of finely ground sodium D-glucarate 6,3-lactone (1.000 g, 4.671 mmol), methanol (30 mL) and dodecamethylenediamine (5.00 g, 25.0 mmol) in a 100 mL round-bottomed flask was refluxed for 3 h at an oil bath temperature of 95° C. During reflux, the amount of insoluble white solid in the reaction mixture appeared to increase. The mixture was cooled to room temperature, the white solid removed by filtration, washed with methanol (2×10 mL), acetone (2×10 mL) and dried at reduced pressure (0.25 torr) at 60° C. for 6 h to give sodium 6-[N-(12′-aminododecyl)]glucaramide-1-ate (1.771 g, 4.273 mmol, 91.5%): mp 198°–200° C.; IR (KBr) 3390 cm$^{-1}$ and 3338 cm$^{-1}$ (N-H, stretch), 3163 cm$^{-1}$ (O-H, stretch), 1653 cm$^{-1}$ (Amide I, C=O), 1630 cm$^{-1}$ (COO$^-$ and amine N-H bend), 1520 (Amide II, N-H bend); $^1$H NMR (acetic acid-D$_6$) δ 4.52 (d, 1H, H-2, $J_{2,3}$=2.40 Hz) , 4.32 (dd, 1H, H-3, $J_{3,4}$=3.12 Hz), 4.15 (dd, 1H, H-4, $J_{4,5}$=5.90 Hz), 4.35 (d, 1H, H-5), 3.30 (t, 2H, H-1′), 3.04 (t, 2H, H-12′), 1.69 (m, 2H, H-2′), 1.55 (m, 2H, H-11′), 1.32 (s, 16H, H-3′, H-4′, H-5′, H-6′, H-7′, H-8′, H-9′, H-10′).

Anal. Calcd for C$_{18}$H$_{35}$O$_7$N$_2$Na (414.5): C, 52.15; H, 8.52; N, 6.76; Na, 5.55. Found: C, 52.20; H, 8.50; N, 6.72; Na, 5.55.

EXAMPLE 9

Head, tail-poly(ethylene-D-glucaramide). A mixture of sodium 6-[N-(2′-aminoethyl)]glucaramide-l-ate (1.000 g, 3.647 mmol) and methanol (10 mL) in a 100 mL round-bottomed flask was cooled in an ice bath and acetyl chloride (1.5 mL, 20 mmol) was added with stirring to dissolve the dimer salt. The solution was stirred at room temperature for 3 h and then concentrated to a syrup which from $^1$H NMR (D$_2$O) appeared to be a mixture of methyl ester and 1,4-lactone at the glucarate C-1 terminals. The $^1$H NMR signals in the carbohydrate region were consistent with the presence of two structures: δ 5.13 (dd, 1H, H-4 in 1,4-lactone, $J_{4,5}$=3.69 Hz), 4.82 (d, 1H, H-2 in 1,4-lactone, $J_{2,3}$=8.94 Hz), 4.73 (d, 1H, H-5 in 1,4-lactone), 4.63 (dd, 1H, H-3 in 1,4-lactone, $J_{3,4}$=7.91 Hz), 4.55 (d, 1H, H-2 in methyl ester, $J_{2,3}$3.02 Hz), 4.31 (d, 1H, H-5 in methyl ester, $J_{4,5}$=4.88 Hz), 4.14 (dd, 1H, H-3 in methyl ester, $J_{3,4}$=5.26 Hz), 3.96 (dd, 1H, H-4 in methyl ester), 3.79 and 3.82 (two —COO—CH$_3$, methyl acetate and methyl ester dimer), 3.57 (q, 2H, —CH$_2$—NH—CO—), 3.39 (s, CH$_3$-OD), 3.34 (s, CH3-OH), 3.18 (q, 2H, —CH$_2$—NH$_2$). The molar ratio of 1,4-lactone and methyl ester from $^1$H NMR spectrum was approximately 1.6:1.0. The syrup was dissolved in methanol (15 mL) and made just basic by careful addition of triethylamine (pH paper). Additional triethylamine (0.5 mL) was added to the solution which was then stirred at room temperature for 30 min. The insoluble solid product was removed by centrifugation, washed with methanol (2×5 mL), acetone (2×5 mL) and dried at reduced pressure at an oil bath temperature of 70° C. to give head, tail-poly(ethylene-D-glucaramide, 0.7532 g, 3.22 mmol, 88.2%): mp 185° C. (dec.); IR (KBr) 3343 cm$^{-1}$ (O-H, stretch), 2950 cm$^{-1}$ (C-H, stretch), 1651 cm$^{-1}$ (Amide I, C=O), 1545 cm$^{-1}$ (Amide II, N-H bend); $^1$H NMR (D$_2$O) δ 4.34 (d, 1H, H-2, $J_{2,3}$=2.3 Hz), 4.10 (s, 1H, H-3), 3.96 (m, 1H, H-4, $J_{4,5}$=5.77 Hz), 4.26 (d, 1H, H-5), 3.43 (s, 4H, H-1' and H-2').

Anal. Calcd for C$_8$H$_{14}$O$_6$N$_2$ (234.21): C, 41.03; H 6.02; N, 11.96. Found: C, 37.94; H, 5.83; N, 10.84.

EXAMPLE 10

Head, tail-poly(tetramethylene-D-glucaramide). A mixture of sodium 6-[N-(4'-aminobutyl)]glucaramide-1-ate (1.000 g, 3.308 mmol) and methanol (10 mL) in 100 mL round-bottomed flask was cooled in an ice bath and acetyl chloride (1.5 mL, 20 mmol) was added with stirring to dissolve the dimer salt. The solution was stirred at room temperature for 3 h and then concentrated to a syrup. The syrup was dissolved in methanol (15 mL) and made just basic by careful addition of triethylamine (pH paper). Additional triethylamine (0.5 mL) was added to the solution which was stirred at room temperature for 30 min. The insoluble solid was removed by filtration, washed with methanol (2×5 mL), acetone (2×5 mL) and dried at reduced pressure at an oil bath temperature of 70° C. to give head, tail-poly(tetramethylene-D-glucaramide) (0.7487 g, 2.85 mmol, 86.3%): mp 185°-188° C. (dec.); IR (KBr) 3312 cm$^{-1}$ (O-H, stretch), 2940 cm$^{-1}$ (C-H, stretch), 1635 cm$^{-1}$ (Amide I, C=O), 1543 cm$^{-1}$ (Amide II, N-H); $^1$H NMR (D$_2$O) δ 4.32 (d, 1H, H-2, $J_{2,3}$=2.87 Hz) 4.09 (dd, 1H, H-3, $J_{3,4}$=4.53 Hz), 3.96 (dd, 1H, H-4, $J_{4,5}$=5.23 Hz), 4.24 (d, 1H, H-5), 3.30 (s, 4H, H-1' and H-4'), 1.59 (s, 4H, H-2' and H-3').

Anal. Calcd for C$_{10}$H$_{18}$O$_6$N$_2$ (262.26): C, 45.80; H, 6.92; N, 10.68. Found: C, 45.72; H, 6.94; N, 10.42.

EXAMPLE 11

Head, tail-poly(hexamethylene-D-glucaramide). A mixture of sodium 6-[N-(6'-aminohexyl)]glucaramide-1-ate (1,000 g, 3.027 mmol) and methanol (10 mL) in a 100 mL round-bottomed flask was cooled in an ice bath and acetyl chloride (1.5 mL, 20 mmol) was added with stirring to dissolve the dimer salt. The solution was stirred at room temperature for 3 h and then concentrated to a syrup. The syrup was dissolved in methanol (15 mL) and made just basic by careful addition of triethylamine (pH paper). Additional triethylamine (0.5 mL) was added to the solution which was stirred at room temperature for 30 min. The insoluble solid product was removed by filtration, washed with methanol (2×5 mL), acetone (2×5 mL) and dried at reduced pressure at an oil bath temperature of 70° C. to give head, tail-poly(hexamethylene-D-glucaramide) (0.802 g, 2.76 mmol, 91.3%): mp 187°-190° C. (dec.-.); IR (KBr) 3313 cm$^{-1}$ (O-H, stretch), 2931 cm$^{-1}$ (C-H, stretch), 1637 cm$^{-1}$ (Amide I, C=O), 1544 cm$^{-1}$ (Amide II, N-H bend); $^1$H NMR (CF$_3$COOD): δ 4.95 (s, 1H, H-2), 4.75 (s, 1H, H-S), 4.60 (d, 1H, H-4), 4.90 (d, 1H, H-5), 3.58 (s, 4H, H-1' and H-6'), 1.78 (s, 4H, H-2' and H-5'), 1.50 (s, 4H, H-3' and H-4').

Anal. Calcd for C$_{12}$H$_{22}$O$_6$N$_2$ (290.31): C, 49.65; H, 7.64; N, 9.65. Found: C, 48.71; H, 7.41; N, 9.56.

EXAMPLE 12

Head, tail-poly(octamethylene-D-glucaramide). A mixture of sodium 6-[N-(8'-aminooctyl)]glucaramide-1-ate (1,000 g, 2.790 mmol) and methanol (10 mL) in a 100 mL round-bottomed flask was cooled in an ice bath and acetyl chloride (1.5 mL, 20 mmol) was added with stirring to dissolve the dimer salt. The solution was stirred at room temperature for 3 h and then concentrated to a syrup. The syrup was dissolved in methanol (15 mL) and made just basic by careful addition of triethylamine (pH paper). Additional triethylamine (0.5 mL) was added to the solution which was stirred at room temperature for 30 min. The insoluble solid product was removed by filtration, washed with methanol (2×5 mL), acetone (2×5 mL) and dried at reduced pressure at an oil bath temperature of 70° C. to give head, tail-poly(octamethylene-D-glucaramide) (0.7612 g, 2.39 mmol, 85.7%): mp 185°-190° C. (dec.); IR (KBr) 3304 cm$^{-1}$ (O-H, stretch), 2926 cm$^{-1}$ (C-H, stretch), 1639 cm$^{-1}$ (Amide I, C=O), 1544 cm$^{-1}$ (Amide II, N-H bend); $^1$H NMR (CF$_3$COOD) δ 4.97 (s, 1H, H-2), 4.77 (s, 1H, H-3), 4.60 (d, 1H, H-4, $J_{4,5}$=5.7 Hz), 4.91 (d, 1H, H-5), 3.58 (s, 4H, H-1' and H-8'), 1.78 (s, 4H, H-2' and H-7'), 1.50 (s, 8H, H-3', H-4', H-5', and H-6').

Anal. Calcd for C$_{14}$H$_{26}$O$_6$N$_2$ (318.36): C, 52.82; H, 8.23; N, 8.80. Found: C, 49.14; H, 7.95; N, 8.65.

EXAMPLE 13

Head, tail-poly(decamethylene-D-glucaramide). A mixture of sodium 6-[N-(10'-aminodecyl)]glucaramide-1-ate (0.5000 g, 1.294 mmol) and methanol (10 mL) in a 100 mL round-bottomed flask was cooled in an ice bath and acetyl chloride (1.5 mL, 20 mmol) was added with stirring to dissolve the dimer salt. The solution was stirred at room temperature for 3 h and then concentrated to a syrup. The syrup was dissolved in methanol (15 mL) and made just basic by careful addition of triethylamine (pH paper). Additional triethylamine (0.5 mL) was added to the solution which was stirred at room temperature for 30 min. The insoluble solid product was removed by filtration, washed with methanol (2×5 mL), acetone (2×5 mL) and dried at reduced pressure at an oil bath temperature of 70° C. to give head, tail-poly(decamethylene-D-glucaramide) (0.3701, 1.068 mmol, 82.5%): mp 193°-196° C. (dec.-.); IR (KBr) 3305 cm$^{-1}$ (O-H, stretch), 2923 cm$^{-1}$ (C-H, stretch), 1640 cm$^{-1}$ (Amide I, C=O), 1546 cm$^{-1}$ (Amide II, N-H); $^1$H NMR (CF$_3$COOD) δ 4.93 (s, 1H, H-2), 4.75 (s, 1H, H-3), 4.58 (d, 1H, H-4, $J_{4,5}$=5.7 Hz), 4.88 (d, 1H, H-5), 3.58 (s, 4H, H-1' and H-10'), 1.71 (s, 4H, H-2' and H-9′), 1.41 (s, 12H, H-3′, H-4′, H-5′, H-6′, H-7′, and H-8′).

Anal. Calcd for $C_{16}H_{30}O_6N_2$ (346.43): C, 55.47; H, 8.73; N, 8.09. Found: C, 56.43; H, 8.94; N, 7.28.

EXAMPLE 14

Head, tail-poly(dodecamethylene-D-glucaramide). A mixture of sodium 6-[N-(12′-aminododecyl)]glucaramide-1-ate (0.5000 g, 1.206 mmol) and methanol (10 mL) in a 100 mL round-bottomed flask was cooled in an ice bath and acetyl chloride (1.5 mL, 20 mmol) was added with stirring to dissolve the dimer salt. The solution was stirred at room temperature for 3 h and then concentrated to a syrup. The syrup was dissolved in methanol (15 mL) and made just basic by careful addition of triethylamine (pH paper). Additional triethylamine (0.5 mL) was added to the solution which was stirred at room temperature for 30 min. The insoluble solid product was removed by filtration, washed with methanol (2×5 mL), acetone (2×5 mL) and dried at reduced pressure at an oil bath temperature of 70° C. to give head, tail-poly(dodecamethylene-D-glucaramide) (0.3861, 1.031 mmol, 85.5%): mp 193°–196° C. (dec.); IR (KBr) 3300 cm$^{-1}$ (O-H, stretch), 2921 cm$^{-1}$ (C-H, stretch), 1641 cm$^{-1}$ (Amide I, C=O), 1547 cm$^{-1}$ (Amide II, N-H bend); NMR (CF$_3$COOD) δ 4.94 (s, 1H, H-2), 4.75 (s, 1H, H-3), 1H 4.58 (d, 1H, H-4, $J_{4,5}$=6.0 Hz), 4.90 (d, 1H, H-5), 3.58 (s, 4H, H-1′ and H-12′), 1.71 (s, 4H, H-2′ and H-11′), 1.45 (s, 16H, H-3′, H-4′, H-5′, H-6′, H-7′, H-8′, H-9′, and H-10′).

Anal. Calcd for $C_{18}H_{34}O_6N_2$ (374.48): C, 57.73; H, 9.15; N, 7.48. Found: C, 56.88; H, 9.16; N, 7.46.

We claim:

1. A process for preparing N-aminohydrocarbylglucaramidate or N-aminoheterohydrocarbyleneglucaramidate alkali metal salts which comprises reacting an alkali metal salt of a glucaromonolactone with a diprimary amine in which the amino nitrogens are attached to aliphatic carbon atoms in a polar organic solvent.

2. The process of claim 1 wherein the alkali metal salt is the sodium salt.

3. A process for preparing N-aminohydrocarbylglucaramidate or N-aminoheterohydrocarbyleneglucaramidate alkali metal salts which comprises reacting an alkali metal salt of a glucaromonolactone with a diprimary amine in which the amino nitrogens are attached to aliphatic carbon atoms in a polar organic solvent and on completion of the reaction recovering the product from the reaction mixture by filtration.

4. The process of claim 3 wherein the alkali metal salt is 396 the sodium salt.

* * * * *